US00PP09794P

United States Patent [19]

McRae et al.

[11] Patent Number: Plant 9,794

[45] Date of Patent: Feb. 4, 1997

[54] LILY PLANT NAMED 'GOLDEN STARGAZER'

[75] Inventors: Edward A. McRae, Sandy, Oreg.; Judith F. McRae, Vancouver, Wash.

[73] Assignee: Van der Salm Bulbfarm Inc., Woodland, Wash.

[21] Appl. No.: 580,617

[22] Filed: Dec. 29, 1995

[51] Int. Cl.[6] ..... A01H 5/00

[52] U.S. Cl. ..... Plt./87.4

[58] Field of Search ..... Plt./87.4

*Primary Examiner*—Howard J. Locker

[57] ABSTRACT

A new variety of hybrid lily plant bearing large outfacing to upfacing flowers of excellent form and long persistence, both on the plant and as cut-flowers. The flowers of the new plant are particularly characterized by their large size and substance, their wide open-bowl form, their outfacing to upfacing orientation, their ascending pedicels, and particularly by their golden yellow coloration, with a flush of deeper gold to orange-gold along the basal midribs and with small, soft red to peach papillae. This combination is completely new in the Oriental and Oriental/Aurelian hybrid lilies. The variety is highly resistant to fusarium disease and shows tolerance of virus. The bulbs may be precooled and forced for cut-flower production under a wide range of light and temperature conditions. The plant is vigorous and is a good grower and propagator.

2 Drawing Sheets

BACKGROUND OF THE INVENTION

Our new variety of lily plant originated as a seedling which first flowered in Woodland, Wash., in 1993. The breeding efforts had as their objective the production of large-flowered Oriental and Oriental/Aurelian hybrids in shades of yellow, gold, and peach, suited to forcing into flower out of season, heretofore unknown in the lily breeding art. Edward A. McRae acchieved the desired objective by pollinating an Oriental/Aurelian hybrid seedling with deep red flowers with a soft gold flowered Oriental/Aurelain hybrid. The unnamed Oriental seedling which was the mother plant of 'Golden Stargazer' was a complex hybrid, produced by embryo-culturing from a cross between an upfacing red Oriental hybrid and a red/gold Oriental/Aurelian hybrid itself originated from embryo culturing. The original maternal crosses came from material unique to his own breeding lines and not available in the trade. Several siblings of this mother plant also produced by embryo culturing from the same complex cross, but all the other siblings clones are sterile. The pollen parent was a complex second-generation Oriental/Aurelian hybrid with large, wide-petalled golden yellow flowers, produced by embryo culturing by Judith Freeman McRae from a cross between an outfacing yellow complex Oriental/Aurelian hybrid and a pendant buff to gold complex Oriental/Aurelian hybrid. Judith Freeman McRae produced both of the original paternal grandparents by embryo-culturing as well, from material unique to her own breeding lines and not available in the trade.

The flowers of our new lily are characterized by an outfacing to upfacing orientation, large size, unusually thick substance, wide open-bowl form with broad tepals, ascending pedicels, and particularly by their golden yellow coloration with flush of deeper orange-gold along the basal midribs and with small, soft red to peach papillae. This combination is completely new in the Oriental and Oriental/Aurelian hybrid lilies. In addition, the clone possesses to a high degree desirable characteristics of hybrid vigor. The clone is a good grower and propagator as observed at Woodland, Wash.

Our new variety of lily plant has been asexually reproduced by us and under our direction at Woodland, Wash. Successive generations produced by natural propagation from bulblets, by bulb scale propagation, and by tissue culturing from bulb scale explants have demonstrated that the novel and distinctive characteristics of our new variety are fixed and hold true under asexual propagation from generation to generation.

DESCRIPTION OF THE DRAWINGS

Our new variety of lily plant is illustrated in the accompanying photographic drawings.

DESCRIPTION OF THE NEW VARIETY

Figure 1:
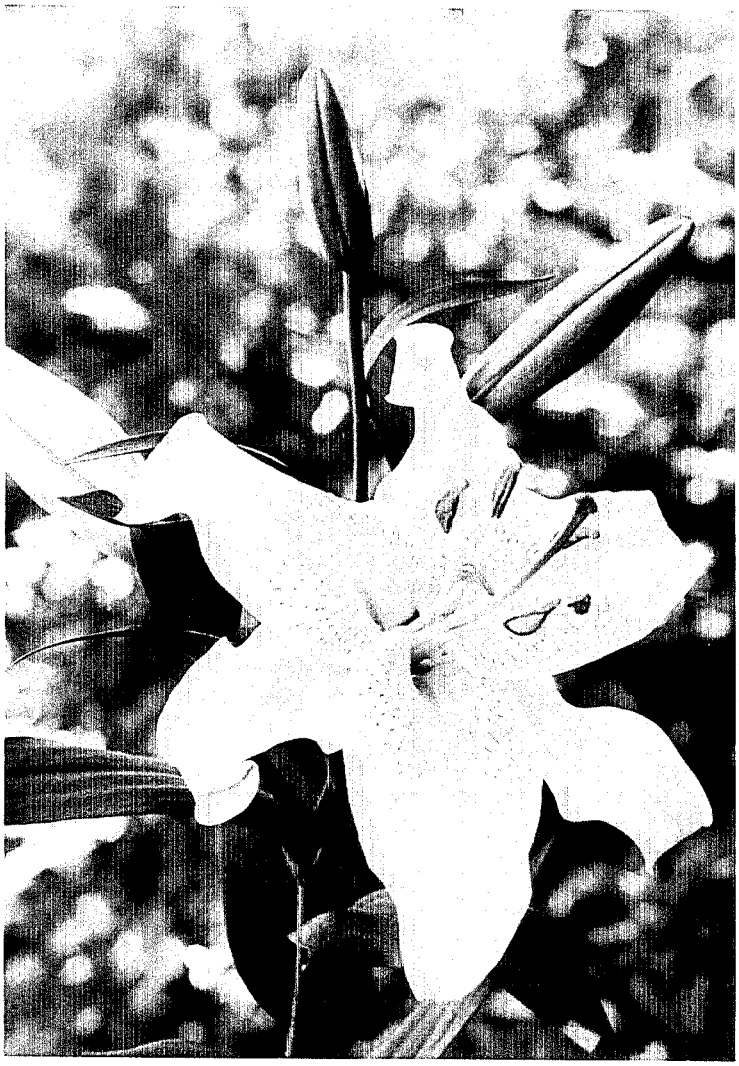
FIG. 1 shows the open bloom in full color and illustrates flower form and orientation, and in particular the novel and distinctive golden yellow coloration with a deeper flush of orange-gold along the midribs and small, soft red to peach papillae, shows tepal arrangement, and the ascending pedicels.
Figure 2:
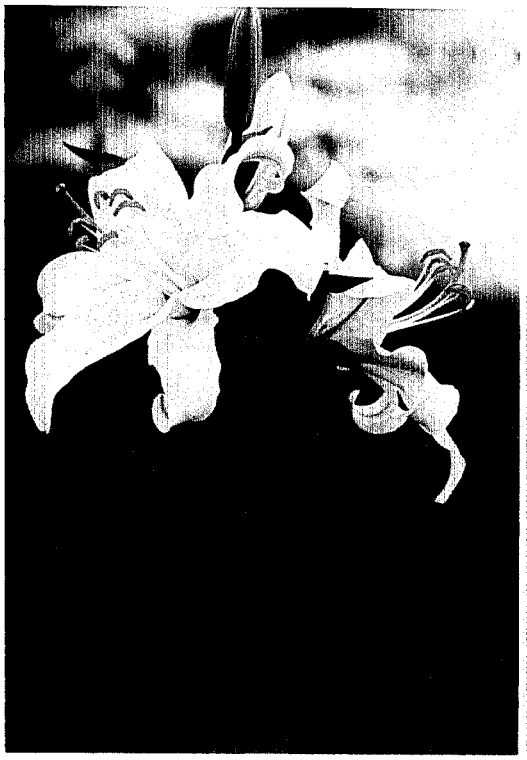
FIG. 2 further illustrates the bloom in various stages of maturity and shows foliage orientation and tepal arrangement.
Figure 3:
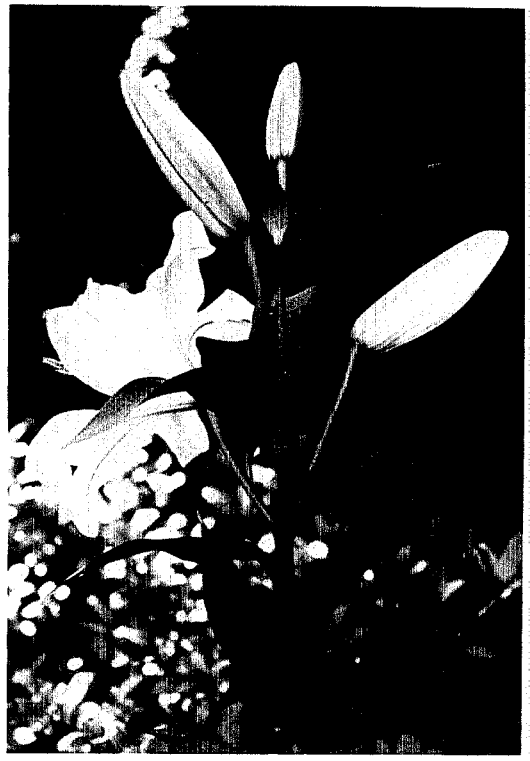
FIG. 3 is similar to FIG. 2, but more clearly shows the ascending pedicels.

The following is a detailed description of my new hybrid lily, with nomenclature according to the *International Lily Register* (Royal Horticultural Society of London, Second Edition, 1969), and with color designations according to the Colour Chart of The Royal Horticultural Society, published by the Society in 1966.

THE PLANT

Origin: Seedling.

Seed parent: Selected unnamed complex Oriental/Aurelian hybrid seedling, produced by embryo culturing.

Pollen parent: Selected unnamed complex Oriental/Aurelian hybrid seedling, produced by embryo culturing.

Commercial classification: Hybrid Lilium clone.

Horticultural classification: Division VII-B, bowl-shaped Oriental hybrid lily, or Division VIII ("to contain all hybrids not provided for in any other division"), according to the Horticultural Classification of Lilies, Royal Horticultural Society of London, 'Golden Stargazer' genetically links Division VII with Division VI; in plant and flower form and in growing characteristics it is distinctly Oriental (Division VII), but it unique color combination shows its Aurelian heritage (Division VI) as well.

Form: Single stem, erect and stately.

Height: 80 to 125 cm from bulbs 14 to 18 cm in circumference, provided their light levels are adequate; low light levels may cause "stretching."

Growth: Vigorous and upright.

Foliage quantity: Abundant.

Size of leaf: Broad, 4 to 7 cm wide×8 to 14 cm long.

Shape of leaf: Lanceolate (pointed).

Texture: Leathery and glossy.

Color: Dark green.

Bulb:

*Size.*—Any size, ranging to 25 cm circumference commercially.

*Color.*—White to pink, with flushes of deep pink or yellow after exposure to light.

THE BUD

Form: Obtuse, ovoid, and long.

Size: 12 to 16 cm long and 10 to 14 cm in circumference just prior to opening.

Opening: Bud opens slowly, in response to morning light; this takes about one hour.

Color: Soft yellow (R.H.S. CC yellow 13 C-D) to soft gold (R.H.S. CC yellow-orange 20 C-D), with soft green midribs, often overlaid with soft pink to plum, just prior to opening.

Peduncle: Average 2 to 4 cm, but it may elongate if light levels are too low or if bulbs have been improperly stored prior to forcing. Color is dark green with plum overlay.

THE FLOWER

Blooming habit: Annually in midseason; flowers once and profusely.

Size: Flowers are large-sized, averaging 20 to 28 cm in diameter, reflexing at the tips on the second day to 18 to 22 cm in diameter. The tepals are broad: outer tepals are 3 to 4 cm wide, and inner tepals are 4.25 to 6 cm wide. The inner tepals overlap slightly.

Borne: In a single racemic inflorescence producing 4 to 8 flowers from a bulb 14 to 16 cm in circumference.

Shape: Forms a broad bowl shape by the second day after opening, with the "bowl" 5 to 6 cm deep. Bowl may open wider to approach a "flat face" form as flower ages.

Tepalage: Typical of genus Lilium, with 6 imbricated tepals.

Tepal:

*Color.*—underlying color is R.H.S. CC yellow 11 A-B, shading to yellow 13 C-D, at margins, a deeper gold R.H.S. CC orange 24 A-C overlays this yellow in a wash 1–3 cm wide on each tepal, deepest at the midrib and extending from the base to the point of tepal recurve. Cool temperatures and bright light levels accentuate the gold tones; low light levels and extreme heat make the color slightly lighter and slightly more yellow.

Spotting.—The basal half of each inner tepal is lightly spotted with small, inconspicuous soft red (R.H.S. CC red 47 A-C) papillae. The papillae are only slightly raised, and they are elongate parallel to the veins of the tepals. The outer tepals have only a few papillae, which are small, inconspicuous, and very soft red to peach gold.

*Nectaries.*—Green nectaries are bordered with a 1–2 mm yellow margin.

*Longevity.*—Tepals stay on stems about three weeks.

Pedicel:

*Length.*—Average 5 to 10 cm long.

*Color.*—Dark green with plum overlay.

*Form.*—Sturdy, flexible, and sharply ascending.

Color changes: Flowers may become slightly lighter and more yellow as they age. Low light levels and extreme heat may cause color to become lighter. Cool temperatures and bright light levels will deepen the color and made it more golden.

Appearance: Flower is shiny.

Disease resistance: The flower and plant are resistant to disease; in particular, they are resistant to Fusarium bulb rot and Botrytis blight.

Fragrance: Slight sweet fragrance.

Lasting quality: The flower is long lasting, both on the plant and as a cut-flower.

THE REPRODUCTIVE ORGANS

Stamens: Arrangement typical of genus Lilium. Six stamens with soft yellow (R.H.S. CC yellow 11 B-C) to soft green filaments 8 to 10 cm long.

Pollen and anthers (dehisced): R.H.S. CC greyed orange 168 A-B.

Pistil: One in number, 10 to 12 cm long; style is light green.

Stigma: Light greyed purple (R.H.S. 186B-D) to light green; medium in size.

Characteristics of ovary: Characteristic of genus Lilium.

THE FRUIT

Fertility: The fruit bears only a few embryos and only rarely fertile seed.

Shape: Ovoid.

Color at maturity: Soft brown, overlaid with soft plum.

Our new variety of Oriental hybrid lily most nearly resembles Lilium 'Star Gazer' (U.S. Plant Pat. No. 4,085) in plant habit, foliar characteristics, and inflorescence. Its flowers are not as completely upfacing, however, and its flower form is a more open bowl, approaching a "flat face" form. Its fragrance is much lighter than that of 'Star Gazer'. Its golden yellow to deeper orange-gold color is distinctly different from 'Star Gazer'; its flower color is somewhat lighter than that of *Lilium henryi* and deeper than that of the gold band of *Lilium auratum.*

We claim:

1. A new and distinctive variety of Oriental hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its outfacing to upfacing buds, its ascending pedicels, and by its unique golden yellow coloration, with deeper orange-gold midrib and soft red papillae, a combination unique among Oriental and Oriental/Aurelian hybrid lilies suited to forcing and to mass commercial cultivation.

* * * * *